(12) United States Patent
Rawls et al.

(10) Patent No.: US 7,715,010 B2
(45) Date of Patent: May 11, 2010

(54) NON-DISPERSIVE ELECTROMAGNETIC RADIATION DETECTOR

(75) Inventors: Nathan C. Rawls, College Station, TX (US); Armando Solar, College Station, TX (US); Kevin D. Morris, Amarillo, TX (US)

(73) Assignee: O.I. Corporation, College Station, TX (US)

( * ) Notice: Subject to any disclaimer, the term of this patent is extended or adjusted under 35 U.S.C. 154(b) by 0 days.

(21) Appl. No.: 12/020,404

(22) Filed: Jan. 25, 2008

(65) Prior Publication Data

US 2008/0198362 A1  Aug. 21, 2008

Related U.S. Application Data

(60) Provisional application No. 60/886,806, filed on Jan. 26, 2007.

(51) Int. Cl.
*G01N 21/00* (2006.01)
(52) U.S. Cl. .................................. 356/437; 356/246
(58) Field of Classification Search ......... 356/432–440, 356/244–246; 250/343
See application file for complete search history.

(56) References Cited

U.S. PATENT DOCUMENTS

| | | | | |
|---|---|---|---|---|
| 4,618,771 A * | 10/1986 | Farren | ........................ | 250/343 |
| 4,914,297 A * | 4/1990 | Wieboldt et al. | ............ | 250/343 |
| 5,125,742 A * | 6/1992 | Wilks, Jr. | ..................... | 356/246 |
| 5,340,986 A * | 8/1994 | Wong | ......................... | 250/343 |
| 5,668,376 A | 9/1997 | Weckstrom et al. | | |
| 5,969,811 A * | 10/1999 | Waller et al. | ................. | 356/246 |
| 2002/0171827 A1 | 11/2002 | Van den Engh | | |
| 2004/0007667 A1 * | 1/2004 | Diekmann et al. | .......... | 250/343 |
| 2006/0073078 A1 | 4/2006 | Peterman, Jr. | | |

OTHER PUBLICATIONS

PCT International Search Report and Written Opinion for International Application No. PCT/US08/052109 dated Jun. 24, 2008.

* cited by examiner

*Primary Examiner*—Hoa Q Pham
(74) *Attorney, Agent, or Firm*—Andrews Kurth LLP; J. Roger Williams, Jr.

(57) ABSTRACT

A flow-through gas cell and a method for passing a sample gas through a flow-through gas cell for spectroscopy are disclosed. In an embodiment, a flow-through gas cell is disclosed. The gas cell includes a substantially cylindrical interior cavity. The interior cavity comprises an inner surface that is reflective. In addition, the gas cell includes a gas inlet and a gas outlet. In the gas cell, a source is disposed on a side of the gas cell, and a detector is disposed on the same side of the gas cell as the source. The source emits electromagnetic radiation, and the detector detects electromagnetic radiation. The gas cell further includes mirrors disposed on opposing ends of the interior cavity.

21 Claims, 3 Drawing Sheets

NON-DISPERSIVE ELECTROMAGNETIC RADIATION DETECTOR

CROSS-REFERENCE TO RELATED APPLICATIONS

This application is a non-provisional application that claims the benefit of U.S. Application Ser. No. 60/886,806 filed on Jan. 26, 2007, which is incorporated by reference herein in its entirety.

STATEMENT REGARDING FEDERALLY SPONSORED RESEARCH OR DEVELOPMENT

Not applicable.

BACKGROUND OF THE INVENTION

1. Field of the Invention

This invention relates to the field of spectroscopy and more specifically to a multi-pass reflective cell for spectroscopy.

2. Background of the Invention

Spectroscopy involves measuring the absorption or radiation of energy by a substance. Typically, gas cells have been used for spectroscopy measurements. The conventional gas cell includes an electromagnetic radiation source optically aligned with a detector. A sample gas is passed through the gas cell with electromagnetic radiation from the source passing through the sample gas in the gas cell to the detector. One potential drawback to this type of measurement is that some substances may exhibit a poor instrumental response either due to the concentration of the substance of interest or due to its lack of interaction with the source energy, which may lead to the inability of the detection system to be able to make an adequate measurement due to the path of the electromagnetic radiation within the gas cell not being of sufficient length. This result may be a consequence of the Beer-Lambert law of spectroscopy as represented by the following equation:

$$-I = I_0 e^{-abc},$$

where I is the final light intensity that reaches the detector, $I_0$ is the incident light from the optical source, a is the molar absorption coefficient that is specific to each sample, b is the pathlength of the light that interacts with the sample, and c is the concentration of the substance in the gas cell.

To overcome such drawbacks, gas cells have been developed with an increase in the length of the electromagnetic radiation interaction path within the gas cell. The increase in length has been accomplished by lengthening the overall tube and thereby increasing the optical pathlength. A disadvantage of this development includes the requirement of a large tube, which may limit the applicability of the device in many instances. In other cases, gas cells (i.e., multi-pass cells) have been developed with mirrored surfaces within the cell body that reflect the electromagnetic radiation in either a circuitous or oscillatory manner within the cell, which may cause the incident optical energy to interact With the substance of interest one or more times. Drawbacks to such gas cells include requirements that the source and detector must be optically aligned since the measurement efficiency of the device is often directly related to the efficiency of the optical energy transfer from the source to the detector. For this same reason, in the case of multi-pass cells, the mirrors used to reflect the light back and forth must be precisely aligned depending upon the overall pathlength desired, which may lead to design difficulties and performance degradation due to any optical misalignments caused by impacts or optical slippage that may occur during normal usage of the device. Further drawbacks include the inefficiencies involved with cables that connect the source and the detector to a circuit board such as a printed circuit assembly. In many optical devices using gas cells, the position of the optical elements often preclude the utilization of multiple circuit boards in order to facilitate the design, which may lead to additional complexity for the overall instrument system.

Consequently, there is a need for an improved gas cell for use in spectroscopy measurements. Further needs include a gas cell with an increased radiation path length. Additional needs include a gas cell that does not require optical alignment of the source and detector. Moreover, needs include the ability to shorten or eliminate electrical connections such that the associated source and detector electronics may be simplified.

BRIEF SUMMARY OF SOME OF THE PREFERRED EMBODIMENTS

These and other needs in the art are addressed in one embodiment by a flow-through gas cell. The gas cell includes a substantially cylindrical interior cavity. The interior cavity comprises an inner surface that is reflective. In addition, the gas cell includes a gas inlet and a gas outlet. In the gas cell, a source is disposed on a side of the gas cell, and a detector is disposed on the same side of the gas cell as the source. The source emits electromagnetic radiation, and the detector detects electromagnetic radiation. The gas cell further includes mirrors disposed on opposing ends of the interior cavity.

In another embodiment, these and other needs in the art are addressed by a method for passing a sample gas through a flow-through gas cell for spectroscopy. The method includes providing a substantially cylindrical interior cavity disposed within the flow-through gas cell, wherein the interior cavity comprises an inner surface that is reflective. The method further includes providing mirrors on opposing ends of the interior cavity, wherein the mirrors comprise a reflective side that is exposed to the interior cavity. In addition, the method includes feeding the sample gas to the interior cavity of the gas cell. Moreover, the method includes providing electromagnetic radiation to the interior cavity, wherein the electromagnetic radiation is provided by a source. The method also includes allowing the electromagnetic radiation to make multiple passes through the sample gas as the electromagnetic radiation is reflected by the inner surface and the mirrors. Additionally, the method includes detecting the electromagnetic radiation with a detector. The detector is disposed on a side of the gas cell, and the source is disposed on the same side of the gas cell as the detector.

The foregoing has outlined rather broadly the features and technical advantages of the present invention in order that the detailed description of the invention that follows may be better understood. Additional features and advantages of the invention will be described hereinafter that form the subject of the claims of the invention. It should be appreciated by those skilled in the art that the conception and the specific embodiments disclosed may be readily utilized as a basis for modifying or designing other embodiments for carrying out the same purposes of the present invention. It should also be realized by those skilled in the art that such equivalent embodiments do not depart from the spirit and scope of the invention as set forth in the appended claims.

BRIEF DESCRIPTION OF THE DRAWINGS

For a detailed description of the preferred embodiments of the invention, reference will now be made to the accompanying drawings in which.

DETAILED DESCRIPTION OF THE PREFERRED EMBODIMENTS

Figure 1:
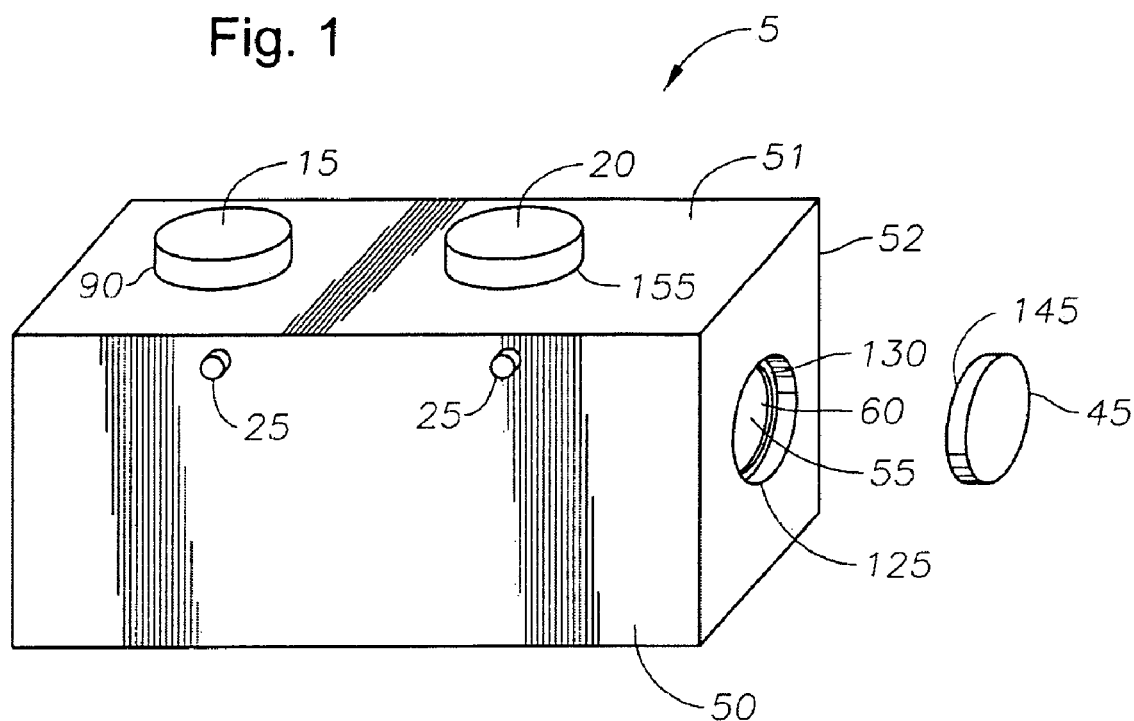
FIG. 1 illustrates a gas cell showing a source, detector, and mirror.
Figure 2:
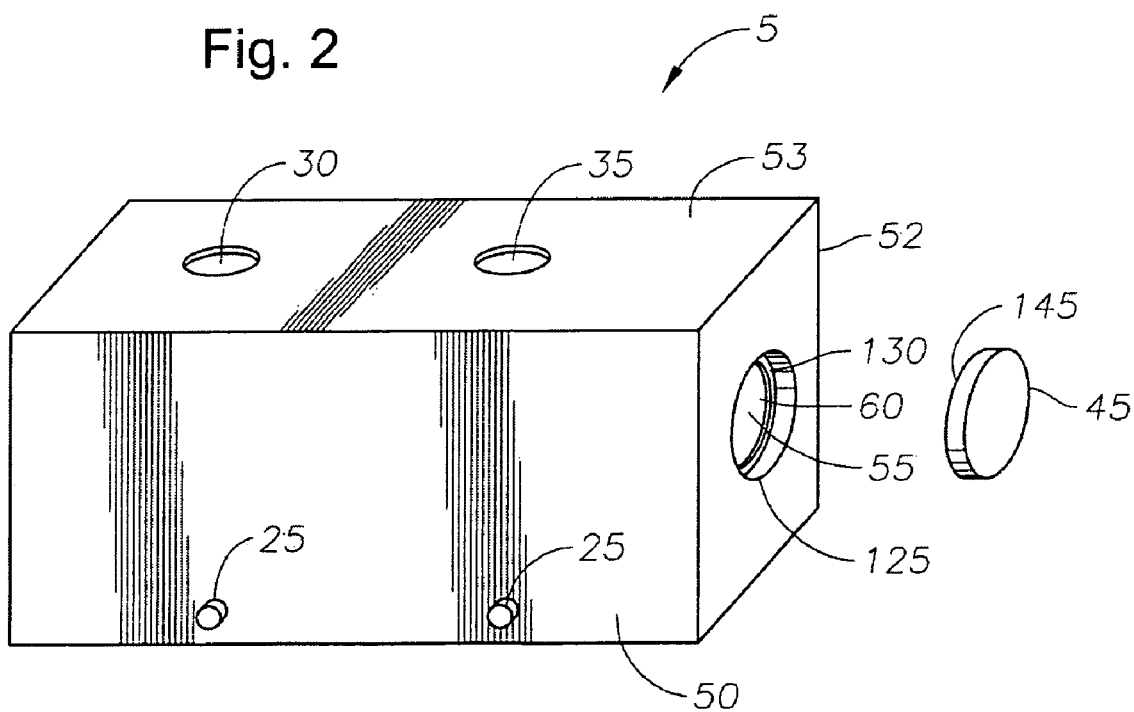
FIG. 2 illustrates a view of the gas cell of FIG. 1 showing the gas cell with a gas inlet, gas outlet, and mirror.

FIGS. 1 and 2 illustrate gas cell 5 comprising source 15, detector 20, gas inlet 30, gas outlet 35, mirror 45, and interior cavity 55. In the embodiments illustrated in FIGS. 1 and 2, source 15 and detector 20 are disposed on the side 51 of gas cell 5 opposite the side 53 of gas cell 5 in which gas inlet 30 and gas outlet 35 are disposed. Source 15 comprises any source that emits electromagnetic radiation suitable for spectroscopy measurements. In embodiments, the forms of electromagnetic radiation emitted by source 15 include ultraviolet radiation, visible light, infrared radiation, and/or any other wavelength. In an embodiment, source 15 emits infrared radiation. Without limitation, commercial examples of suitable sources 15 include PULSIR high power infrared source commercially available from ICX Precision Photonics and HELIOWORKS model EP-3963 pulsable IR source distributed by Boston Electronics. Source 15 may be modulated or may be operated without modulation. In an embodiment, source 15 is modulated. Source 15 may be modulated by any method suitable for spectroscopy measurements. For instance, modulation methods include electrical pulsation, chopper modulation (e.g., a rotating chopper wheel), and electro-optical modulation (e.g., a Pockels cell). In an embodiment, source 15 is modulated by electrical pulsation at any suitable frequency. In embodiments, source 15 has about a 1 hertz pulse. In an embodiment, source 15 does not comprise a lens. Without being limited by theory, a lens is not required because of the multiple pass arrangement of gas cell 5. In alternative embodiments, source 15 comprises a lens.

Detector 20 comprises any detector suitable for detecting electromagnetic radiation. Without limitation, commercial examples of suitable detectors 20 include pyroelectric detectors provided by Eltec, Instruments Inc.; Model 2MC Au thermopile detectors manufactured by Dexter Research Center, Inc.; MCT (mercury-cadmium-telluride) detectors manufactured by Vigo Industries and distributed by Boston Electronics; and S9055 PIN photodiodes and SP9251-10 AVD's (Avalanche photodiodes) manufactured by Hamamatsu. In an embodiment, source 15 and detector 20 are disposed on the same side of gas cell 5. In such an embodiment, source 15 and detector 20 may be disposed at any location on any side of gas cell 5. For instance, as illustrated in FIG. 1, source 15 and detector 20 are disposed on side 51 of gas cell 5. In alternative embodiments (not illustrated), source 15 and detector 20 are disposed on different sides of gas cell 5.

As shown in FIGS. 1 and 2, gas cell 5 is a flow-through cell having an interior cavity 55. Interior cavity 55 has a substantially cylindrical shape and is disposed lengthwise in gas cell 5. Gas cell 5 has two mirror openings 125 that allow access to interior cavity 55 from each lengthwise end 52 of gas cell 5. For illustration purposes only, one mirror opening 125 and lengthwise end 52 of gas cell 5 are shown in FIG. 1. Gas cell 5 further comprises a removable mirror 45 disposed in each mirror opening 125. For illustration purposes, mirror 45 is shown separated from mirror opening 125 in FIG. 1. Mirror 45 has a reflective side 145 that faces interior cavity 55 and is exposed to interior cavity 55. Reflective side 145 comprises material suitable for reflecting electromagnetic radiation. In an embodiment, reflective side 145 comprises aluminum, silver, copper, gold, or combinations thereof; alternatively aluminum and/or gold; and alternatively gold. In some embodiments, reflective side 145 comprises a material suitable for reflecting electromagnetic radiation disposed on another material. The material may be disposed on another material by any suitable method. Examples of suitable methods include coating, plating, and the like. For instance, reflective side 145 may comprise gold plated on aluminum. In an embodiment, mirror 45 is sufficiently disposed in mirror opening 125 to allow mirror 45 to be in contact with mirror stop 130. Mirror stop 130 has a diameter smaller than the diameter of mirror opening 125. Mirror stop 130 prevents movement of mirror 45 into interior cavity 55.

Gas cell 5 may be comprised of any material suitable for use in spectroscopy. In an embodiment, gas cell 5 comprises aluminum, silver, copper, gold, or combinations thereof. Inner surface 60 of interior cavity 55 is a reflective surface suitable for reflecting electromagnetic radiation. In an embodiment, inner surface 60 comprises aluminum, silver, copper, gold, or combinations thereof; alternatively gold and/or aluminum; and alternatively aluminum. In some embodiments, inner surface 60 comprises a material suitable for reflecting electromagnetic radiation disposed on another material. The material may be disposed on another material by any suitable method. Examples of suitable methods include coating, plating, and the like. For instance, interior cavity 55 may be comprised of aluminum, and inner surface 60 may comprise gold plated on the aluminum of interior cavity 55.

Figure 3:
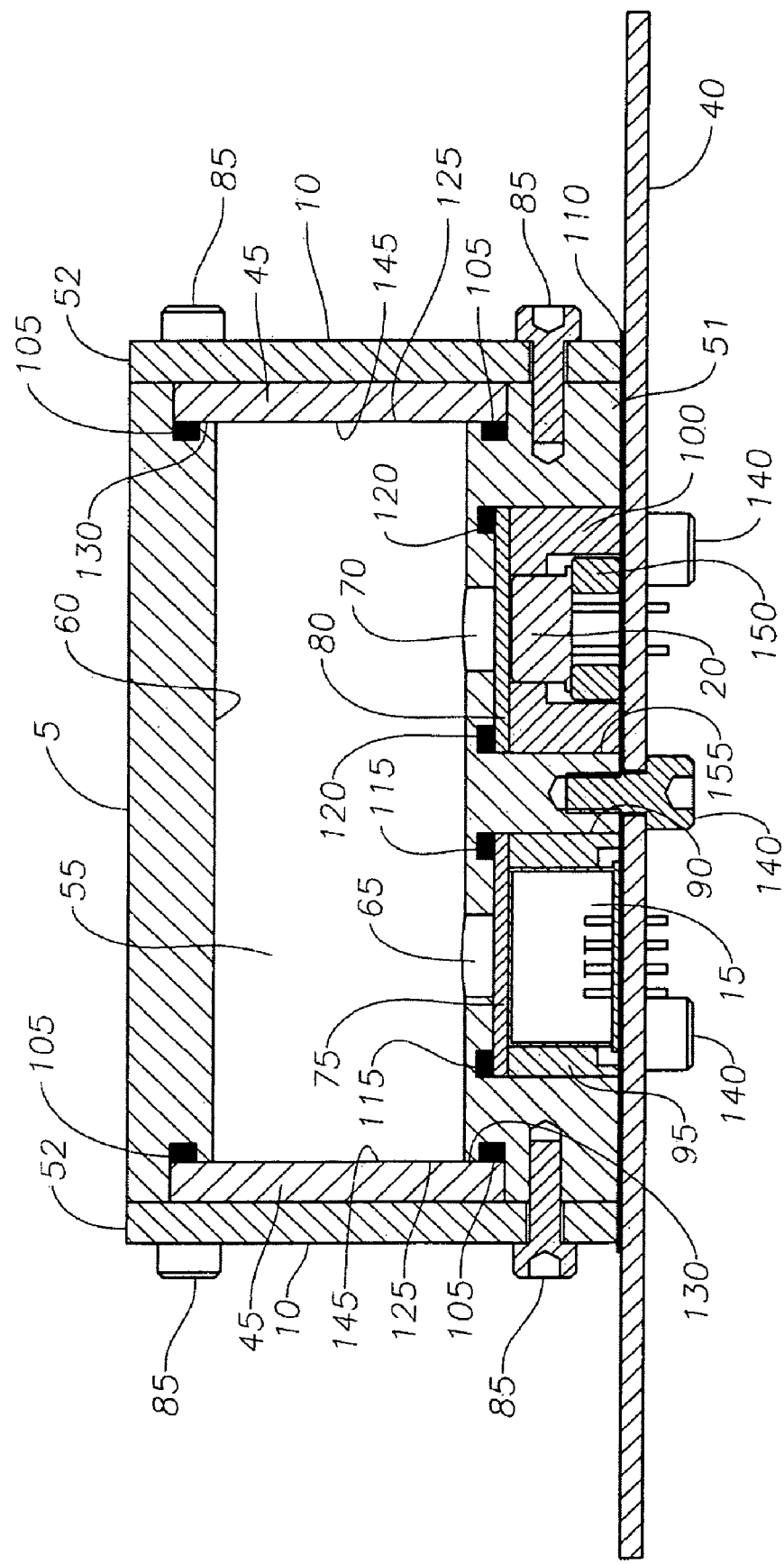
FIG. 3 illustrates a side view of a gas cell and circuit board with a side of the gas cell removed for illustrative purposes.

In an embodiment as illustrated in FIGS. 1 and 2, gas cell 5 has a rectangular shape. However, it is to be understood that gas cell 5 is not limited to a rectangular shape but may have any other shape suitable for spectroscopy. For instance, in alternative embodiments, gas cell 5 may have a cylindrical shape. In some embodiments, gas cell 5 has a non rectangular shape with a substantially flat side 51 on which source 15 and detector 20 are disposed. Without being limited by theory, gas cell 5 having a configuration with a substantially flat side 51 (e.g., gas cell 5 having a substantially rectangular shape) facilitates attachment of flat side 51 of gas cell 5 to a circuit board 40 (e.g., as illustrated in FIG. 3). For instance, electrical cables, connectors, and the like of source 15 and detector 20 may be proximate to circuit board 40 whereas inefficiencies may be involved if such cables, connectors, and the like extend from another side of gas cell 5 and therefore at a location more remote from circuit board 40.

As further illustrated in FIG. 1, gas cell 5 comprises gas purge inlets 25 in side 50. Gas purge inlets 25 allow purge gas to be provided to source opening 90 and detector opening 155. The purge gas comprises any gas free or substantially free of the sample gas (e.g., gas being measured). For instance, if carbon dioxide is the gas being measured in the sample gas, the purge gas contains substantially no carbon dioxide gas. Gas purge inlets 25 may be of sufficient size to allow purge gas to flow around source 15 and detector 20. The purge gas may exit gas cell 5 through purge gas outlets (not illustrated). In the embodiment as shown in FIG. 1, source opening 90 and detector opening 155 each have one supplying gas purge inlet 25. In alternative embodiments (not illustrated), source opening 90 may have more than one supplying gas purge inlet 25, and detector opening 155 may have more than one supplying gas purge inlet 25. In other alternative embodiments (not illustrated), a gas purge is not provided to source opening 90 and/or detector opening 155. In some alternative embodiments, purge gas may not be provided to source opening 90 and/or detector opening 155 if ambient gases cause no analytical interference. In an embodiment, purge gas is fed to gas purge inlet 25 at a rate sufficient to remove any gas from the respective source opening 90 and detector opening 155 and thereby facilitates the prevention of such gas from seeping to interior cavity 55. In some embodiments, purge gas is fed at a rate of about 20 ml/min to about 250 ml/min. In other alternative embodiments (not illustrated), a sufficient vacuum may be applied to the environment around gas cell 5 such that interfering gases may not interact with detector 20. In other alternative embodiments, a chemical sorbent may be sufficiently located at gas cell 5 to eliminate an interfering gas.

As shown in FIG. 2, gas cell 5 further comprises gas inlet 30 and gas outlet 35. Gas inlet 30 is sufficient to allow the sample gas to be fed to interior cavity 55, and gas outlet 35 is suitable to allow the sample gas to exit interior cavity 55. The sample gas comprises the gas to be measured (e.g., carbon dioxide). It is to be understood that gas cell 5 is not limited to one gas inlet 30 and one gas outlet 35 but in alternative embodiments may include more than one gas inlet 30 and/or more than one gas outlet 35. In the embodiments shown in FIGS. 1 and 2, gas inlet 30 and gas outlet 35 are disposed in the side 53 opposite to the side 51 of source 15 and detector 20. In alternative embodiments (not illustrated), gas inlet 30 and gas outlet 35 may be disposed on any side of gas cell 5. In further embodiments (not illustrated), gas inlet 30 and gas outlet 35 are on different sides of gas cell 5. In other embodiments (not illustrated), gas cell 5 may be used for measurements without a flow of gas through gas cell 5. For instance, a measurement used as a background may be accomplished without a gas flow through gas cell 5. In other embodiments (not illustrated), gas cell 5 may include sufficient perforations that ambient air may pass freely through gas cell 5 to allow gas cell 5 to measure ambient gases in the environment near gas cell 5.

FIG. 3 illustrates a side view of an embodiment of gas cell 5 attached to a circuit board 40. Circuit board 40 may include any circuit board suitable for use in spectroscopy. It is to be understood that FIG. 3 is illustrated with a side 50 removed for illustration purposes only. As shown, side 51 is secured to circuit board 40 in a location on circuit board 40 suitable for the electrical connection of source 15 and/or detector 20 to circuit board 40. Gas cell 5 may be secured to circuit board 40 by gas cell securing means 140. Gas cell securing means 140 may include any suitable means by which gas cell 5 may be secured to circuit board 40. Without limitation, examples of suitable gas cell securing means 140 include screws, pins, adhesives, and the like. In an embodiment as shown in FIG. 3, gas cell securing means 140 comprise screws. As further shown, a circuit board seal 110 is disposed between gas cell 5 and circuit board 40. Circuit board seal 110 may be any seal suitable for withstanding the compressive load of securing gas cell 5 to circuit board 40 and sufficient to facilitate a gas sealing action to gas cell 5. For instance, circuit board seal 110 may be a mechanical seal such as a gasket. In alternative embodiments (not illustrated), gas cell 5 does not include circuit board seal 110. In some alternative embodiments (not illustrated), gas cell 5 includes insulating tape instead of circuit board seal 100. Gas cell securing means 140 secures circuit board seal 110 between gas cell 5 and circuit board 40. In alternative embodiments (not illustrated), a circuit board seal 110 is not disposed between gas cell 5 and circuit board 40. Moreover, gas cell 5 has a source opening 90 in which source 15 may be disposed. Gas cell 5 may also include a source spacer ring 95 disposed in source opening 90. Source 15 is disposed in source spacer ring 95. Without limitation, source spacer ring 95 facilitates positioning of source 15, provides thermal insulation to source 15, and provides pressure on source window 75 to form a seal with source window seal 115.

As illustrated in FIG. 3, gas cell 5 has source optical opening 65, which is an opening between interior cavity 55 and source 15 that allows electromagnetic radiation from source 15 to flow into interior cavity 55. A source window 75 is disposed in source opening 90 between source 15 and source optical opening 65. Source window 75 comprises a material suitable for allowing electromagnetic radiation to flow from source 15 to interior cavity 55 (e.g., transparent to wavelength of interest). For instance, source window 75 may be composed of calcium fluoride, quartz, zinc selenide, germanium, and the like. In an embodiment, source window 75 is transparent to infrared radiation. In some embodiments, source window 75 also provides a seal for interior cavity 55 by preventing gas from entering and exiting interior cavity 55 through source optical opening 65. A further seal for interior cavity 55 is provided by source window seal 115. Source window seal 115 may be any seal suitable for providing a seal to interior cavity 55 and source optical opening 65 such as an o-ring.

As further illustrated in FIG. 3, gas cell 5 includes detector opening 155 in which detector 20 is disposed. In addition, gas cell 5 may also include a detector spacer ring 100 disposed in detector opening 155. Detector 20 is disposed in detector spacer ring 100. Without limitation, detector spacer ring 100 facilitates alignment of detector 20, provides thermal insulation to detector 20, and provides pressure on detector window 80 to form a seal with detector window seal 120. Moreover, gas cell 5 has detector optical opening 70, which is an opening between interior cavity 55 and detector 20 that allows electromagnetic radiation from interior cavity 55 to flow into detector 20 for detection. A detector window 80 is disposed in detector opening 155 between detector 20 and detector optical opening 70. Detector window 80 comprises a material suitable for allowing electromagnetic radiation to flow from interior cavity 55 to detector 20 (e.g., transparent to wavelength of interest). For instance, detector window 80 may be composed of calcium fluoride, quartz, zinc selenide, germanium, and the like. In an embodiment, detector window 80 is transparent to infrared radiation. In some embodiments, source window 75 and detector window 80 comprise substantially the same materials. In embodiments, detector window 80 provides a seal for interior cavity 55 by preventing gas from entering and exiting interior cavity 55 through detector optical opening 70. A further seal for interior cavity 55 is provided by detector window seal 120. Detector window seal 120 may be any seal suitable for providing a seal to interior cavity 55 and detector optical opening 70 such as an o-ring. In some embodiments as shown in FIG. 3, gas cell 5 also includes a detector spacing seat 150. Detector seat 150 may include any suitable mechanism for providing physical support to detector 20. Without limitation, examples of suitable detector seats include washers and nuts.

As further illustrated in FIG. 3, gas cell 5 has mirror openings 125 on opposing sides 52. In an embodiment, mirror openings 125 allow access to interior cavity 55, which allows for polishing of inner surface 60 and for cleaning of the same surface. It is to be understood that inner surface 60 is sufficiently polished to provide a surface suitable for reflecting electromagnetic radiation. Mirror openings 125 are manufactured during the machining of gas cell 5 for the fabrication of interior cavity 55. Mirrors 45 are disposed in mirror openings 125 with reflective side 145 facing interior cavity 55 and in contact with mirror stop 130. Mirror 45 also provides a seal to interior cavity 55. In some embodiments as illustrated in FIG. 3, gas cell 5 may have a mirror seal 105 disposed between reflective side 145 and gas cell 5. Mirror seal 105 may be any seal suitable for providing a seal to interior cavity 55 such as an o-ring.

Plates 10 are secured to gas cell 5 by plate securing means 85. Plate securing means 85 includes any suitable means by which plate 10 may be secured to gas cell 5. Without limitation, examples of suitable plate securing means 85 include screws, pins, adhesives, and the like. In an embodiment as shown in FIG. 3, plate securing means 85 comprises screws. Gas cell 5 may include any number of plate securing means 85 suitable for securing plate 10 to gas cell 5. Without being limited by theory, securing plate 10 to gas cell 5 facilitates the seal of interior cavity 55 by preventing unwanted movement of mirror 45.

Figure 4:
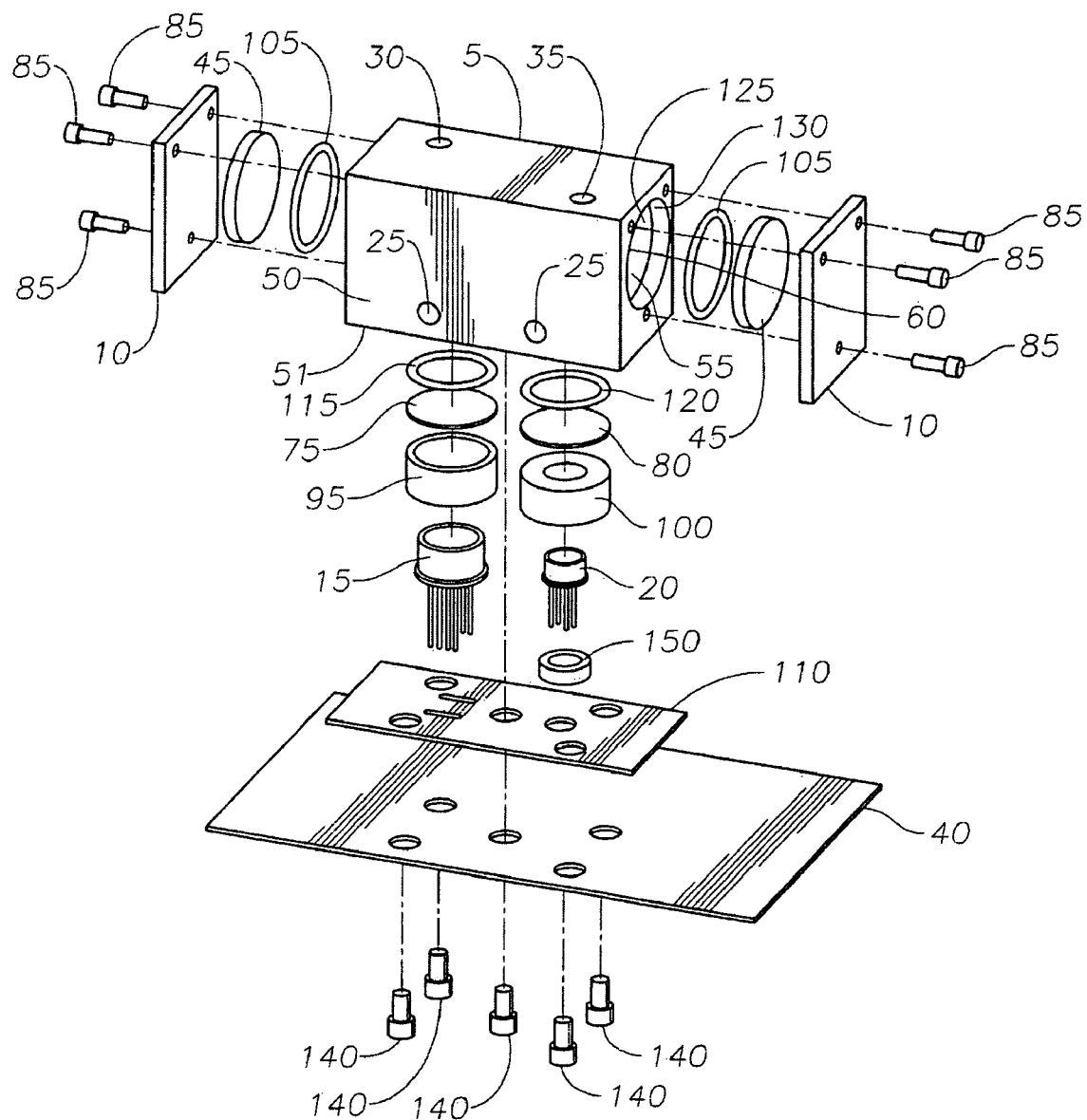
FIG. 4 illustrates an exploded view of the gas cell and circuit board of FIG. 3.

FIG. 4 illustrates an exploded view of gas cell 5 with circuit board 40. As illustrated, three plate securing means 85 comprising screws are used to secure each plate 10 to gas cell 5, but it is to be understood that gas cell 5 may have more or less than three plate securing means 85 for each plate 10. As further illustrated, five gas cell securing means 140 comprising screws are used to secure circuit board 40 and circuit board seal 110 to gas cell 5, but it is to be understood that gas cell 5 may have more or less than five gas cell securing means 140.

In an embodiment, source 15 and detector 20 are not optically aligned. For instance, as shown in the embodiments of FIGS. 1-4, source 15, detector 20, and interior cavity 55 (e.g., containing the sample gas volume) are not on the same axis. It is to be understood that optically aligned refers to focusing electromagnetic radiation from source 15 to detector 20 through a well-defined path. Without being limited by theory, source 15 and detector 20 are not required to be optically aligned because the cylindrical configuration of interior cavity 55 with reflective inner surface 60 and mirrors 45 enable gas cell 5 to act as an optical cavity. Therefore, the configuration of gas cell 5 provides a multiple reflective arrangement without source 15, detector 20, and interior cavity 55 in optical alignment. Further, without being limited by theory, electromagnetic radiation provided to interior cavity 55 by source 15 is absorbed, scattered, exits interior cavity 55 through source optical opening 65, or exits interior cavity 55 through detector optical opening 70 for detection by detector 20. Moreover, the configuration of gas cell 5 as embodied in FIGS. 1-4 provides an increased path length for the electromagnetic radiation, which allows for an increased absorbance. Without limitation, due to the random bouncing of source 15 electromagnetic radiation inside gas cell 5, the path length is not unique. Instead, the path length is rather an ensemble of path lengths that on average account for an increased path length many times larger than any physical dimension of gas cell 5. In an alternative embodiment, the sample may emit light rather than absorb light, which includes exciting the sample with light of a particular wavelength and detecting emitted fluorescence or other luminescence by means of the multi-pass cell optical characteristics of gas cell 5.

In an embodiment of the operation of gas cell 5 as illustrated in FIGS. 1-4, a constant flow of a sample gas is fed to interior cavity 55 through gas inlet 30. Source 15 provides electromagnetic radiation (e.g., infrared radiation) through source optical opening 65 to interior cavity 55 wherein the electromagnetic radiation is multiply reflected by inner surface 60 and mirrors 45, which provides multiple passes of the electromagnetic radiation through the sample gas. The electromagnetic radiation exits the interior cavity 55 through detector optical opening 70 for detection by detector 20.

Although the present invention and its advantages have been described in detail, it should be understood that various changes, substitutions and alterations may be made herein without departing from the spirit and scope of the invention as defined by the appended claims.

What is claimed is:

1. A flow-through gas cell, comprising:
a substantially cylindrical interior cavity, wherein the interior cavity comprises an inner surface, and wherein the inner surface is reflective;
a gas inlet and a gas outlet;
a source disposed on a side of the gas cell and a detector disposed on the same side of the gas cell the source, wherein the source emits electromagnetic radiation and the detector detects electromagnetic radiation;
a source optical opening that allows electromagnetic radiation from the source to flow into the interior cavity;
a detector optical opening that allows electromagnetic radiation from the interior cavity to flow to the detector;
a source window disposed between the source and the source optical opening and a detector window disposed between the detector and the detector optical opening; and
mirrors disposed on opposing ends of the interior cavity.

2. The flow-through gas cell of claim 1, wherein the gas inlet and the gas outlet are disposed on an opposite side of the gas cell from the source and the detector.

3. The flow-through gas cell of claim 1, wherein the electromagnetic radiation comprises infrared radiation.

4. The flow-through gas cell of claim 1, wherein the source is modulated.

5. The flow-through gas cell of claim 1, wherein the mirrors comprise a reflective side, and wherein the reflective side is exposed to the interior cavity.

6. The flow-through gas cell of claim 1, wherein the opposing ends of the interior cavity each comprise a mirror opening, wherein a mirror is disposed in each mirror opening.

7. The flow-through gas cell of claim 6, wherein the mirror opening comprises a mirror stop with a diameter sufficient to prevent movement of the mirror into the interior cavity.

8. The flow-through gas cell of claim 1, wherein the gas cell comprises aluminum, silver, copper, gold, or combinations thereof.

9. The flow-through gas cell of claim 1, wherein the inner surface comprises aluminum, silver, copper, gold, or combinations thereof.

10. The flow-through gas cell of claim 1, wherein the gas cell comprises a rectangular shape, and wherein the substantially cylindrical interior cavity is disposed longitudinally within the gas cell.

11. The flow-through gas cell of claim 1, wherein the side of the gas cell on which the source and the detector are disposed comprises a substantially flat side.

12. The flow-through gas cell of claim 1, wherein the gas cell is attached to a circuit board.

13. The flow-through gas cell of claim 12, wherein the side of the gas cell on which the source and the detector are disposed is attached to the circuit board.

14. The flow-through gas cell of claim 1, wherein the gas cell comprises a source opening in which the source is disposed, and the gas cell comprises a detector opening in which the detector is disposed.

15. The flow-through gas cell of claim 14, further comprising a gas purge, wherein the gas purge is provided to the source opening and/or to the detector opening.

16. The flow-through gas cell of claim 1, wherein the detector and the source are not optically aligned.

17. The flow-through gas cell of claim 1, wherein at least one of the detector and the source is mounted on the side of the gas cell.

18. The flow-through gas cell of claim 1, further comprising a mirror opening which provides access to the interior cavity, wherein at least one of the mirrors is disposed in the mirror opening.

19. The flow-through gas cell of claim 1, wherein the source and the detector are not aligned with an axis of the interior cavity.

20. A method for passing a sample gas through a flow-through gas cell for spectroscopy, comprising:
  (a) providing a substantially cylindrical interior cavity disposed within the flow-through gas cell, wherein the interior cavity comprises an inner surface, and wherein the inner surface is reflective;
  (b) providing mirrors on opposing ends of the interior cavity, wherein the mirrors comprise a reflective side, and wherein the reflective side is exposed to the interior cavity;
  (c) providing in the flow-through gas cell a source optical opening that allows electromagnetic radiation from the source to flow into the interior cavity, a detector optical opening that allows electromagnetic radiation from the interior cavity to flow to the detector, a source window disposed between the source and the source optical opening and a detector window disposed between the detector and the detector optical opening; and
  (d) feeding the sample gas to the interior cavity of the gas cell;
  (e) providing electromagnetic radiation to the interior cavity, wherein the electromagnetic radiation is provided by a source;
  (f) allowing the electromagnetic radiation to make multiple passes through the sample gas as the electromagnetic radiation is reflected by the inner surface and the mirrors; and
  (g) detecting the electromagnetic radiation with a detector, wherein the detector is disposed on a side of the gas cell and the source is disposed on the same side of the gas cell as the detector.

21. The method of claim 20, wherein the source and the detector are not optically aligned.

* * * * *